United States Patent [19]

Batelaan et al.

[11] Patent Number: 5,434,208
[45] Date of Patent: Jul. 18, 1995

[54] OPTICALLY NON-LINEAR ACTIVE WAVEGUIDING MATERIAL COMPRISING A DOPANT HAVING MULTIPLE DONOR-N-ACCEPTOR SYSTEMS

[75] Inventors: Jan G. Batelaan, Arnhem; Johannes F. J. Engbersen, Ede; Erik Kelderman, Enschede; David N. Reinhoudt, Hengelo; Willem Verboom, Vriezenveen, all of Netherlands

[73] Assignee: Akzo Nobel N.V., Arnhem, Netherlands

[21] Appl. No.: 88,140

[22] Filed: Jul. 7, 1993

[30] Foreign Application Priority Data

Jul. 10, 1992 [NL] Netherlands .................. 9201241

[51] Int. Cl.⁶ .................. C08K 5/13; H01C 13/00
[52] U.S. Cl. .................. 524/288; 524/289; 524/290; 524/291; 524/325; 524/345; 524/349; 524/367; 524/368; 252/501.1; 359/321
[58] Field of Search ............... 524/325, 345, 349, 288, 524/289, 291, 367, 368; 528/487, 491, 492; 252/501.1; 359/321

[56] References Cited

U.S. PATENT DOCUMENTS

| | | | |
|---|---|---|---|
| 4,617,336 | 10/1986 | Pastor et al. | 524/291 |
| 4,755,326 | 7/1988 | Liepins et al. | 252/518 |
| 4,957,960 | 9/1990 | Harris et al. | 524/288 |

FOREIGN PATENT DOCUMENTS

| | | |
|---|---|---|
| 62-265250 | 11/1987 | Japan . |
| 1059222 | 3/1989 | Japan . |
| 2124863 | 5/1990 | Japan . |
| 4015232 | 1/1992 | Japan . |
| 2189624 | 10/1987 | United Kingdom . |

OTHER PUBLICATIONS

"syn-1,2-Dialkylated Calix[4]arenes: General Intermediates in the NaH/DMF Tetraalkylation of Calis[4]arenes"; *Tetrahedron Letters*; vol. 32, No. 23, pp. 2675-2678 (1991), Groenen, Ruel, Casnati, Timmerman, Verboom, Harkema, Pochini, Ungaro and Reinhoudt.
"Calixarenes 12, The Synthesis of Functionalized Calixarenes"; *Tetrahedron Letters*; vol. 42, No. 6, pp. 1633-1640 (1986). Gutsche and Lin.
"Autoaccelerative Diazo Coupling with Calix[4]arene: Unusual Cooperativity of the Calixarene Hydroxy Groups", *J. Chem. Soc.* Perkin Trans. I, pp. 195-196, (1989), Shinkai, Araki, Shibata, and Manabe.
"Ipso Nitration of p-tert-Butylcalix[4]arenes", *J. Org. Chem.*, vol. 57, No. 4, pp. 1313-1316, (1992), Verboom, Durie, Egberink, Asfari and Reinhoudt.
"Diazo-Coupling Reactions with Calix[4]arene . . . ", *Chemistry Letters*, Tokyo, Japan, pp. 931-934 (1989), Shinkai, Araki, Shibata, Tsugawa and Manabe.
"Novel Calixarenes in thin films for efficient second harmonic generation", *Applied Physics Letters*, vol. 62, Apr. 26, 1993, No. 17, pp. 2015-2017, Heesink, et al.

*Primary Examiner*—Tae H. Yoon
*Attorney, Agent, or Firm*—Richard P. Fennelly; Louis A. Morris

[57] ABSTRACT

The invention relates to an optically non-linear active waveguiding material comprising an optically transparent polymer and a non-linear optical dopant comprising more than one donor-π-acceptor unit.

Dopants comprising more than one donor-π-acceptor unit, especially dopants in which the donor-π-acceptor units are positioned in a cyclic group, have a high hyperpolarizability and a charge-transfer absorption band wavelength which is about the same as that of dopants with only one donor-π-acceptor unit.

Especially suitable dopants for use are calix(4)arenes. These are provided with acceptor groups at the upper rim and with donor groups at the lower rim. In addition to having excellent hyperpolarizability, these compounds were found to be readily soluble in host polymers, such as polymethylene (meth) acrylate and polystyrene. Because of their charge-transfer absorption band at a low wavelength, optically non-linear active waveguiding structures containing such dopants are suitable for use as frequency doublers.

The invention further relates to hitherto undisclosed calix(4)arenes functionalized with nitrostilbene groups, cyanostilbene groups, sulfor stilbene groups, sulfonate stilbene groups, azobenzenes or benzylidene aniline compounds.

1 Claim, No Drawings

OPTICALLY NON-LINEAR ACTIVE WAVEGUIDING MATERIAL COMPRISING A DOPANT HAVING MULTIPLE DONOR-N-ACCEPTOR SYSTEMS

BACKGROUND OF THE INVENTION

1. Field of the Invention

The invention relates to an optically non-linear active waveguiding material comprising an optically transparent polymer and an optically non-linear active dopant, comprising a donor-$\pi$-acceptor unit.

2. Description of the Prior Art

In optically non-linear materials, under the influence of an external field of force (such as an electric field of force E), non-linear polarization occurs. In the case of organic molecules this is called an induced dipole moment. The induced dipole moment ($\mu_{ind}$) may be represented as follows:

$$\mu_{ind} = \alpha E + \beta EE + \gamma EEE + \qquad [1]$$

wherein $\alpha$ stands for the linear hyperpolarizability, $\beta$ represents the (non-linear) hyperpolarizability, $\gamma$ stands for the second hyperpolarizability, etc.

Non-linear electric polarisation ($\beta$ and $\gamma$ do not equal zero) may give rise to a number of optically non-linear phenomena, such as frequency doubling and the Pockels effect. By utilizing these phenomena it is possible to employ this material in optically active waveguiding structures such as optical switches, frequency doublers, etc.

To this end the organic optically non-linear active material is to be applied to a substrate in the form of thin layers. Three polymer systems are suitable for this purpose: guest-host polymer systems, functionalized polymers, and polymer networks. In the first system, which is by far the easiest to prepare, an optically transparent polymer contains optically non-linear active compounds as dopants.

Such an optically non-linear active waveguiding material is disclosed in GB 2 189 624, where an optically transparent polymer is impregnated with an optically non-linear dopant comprising a donor-$\pi$-acceptor unit.

Most organic optically non-linear active compounds owe their nonlinear optical properties to so-called donor-$\pi$-acceptor units. By this term are meant, groups composed of an electron-donating group and an electron-accepting group coupled to the same conjugated $\pi$-system. Compounds containing such a material were found to have a comparatively high hyperpolarizability ($\beta$).

For several years now efforts have been made in industry to prepare materials of a higher hyperpolarizability, for instance by expanding the donor-$\pi$-acceptor units. While the hyperpolarizability is thus increased, there is, simultaneously, a shift in the charge-transfer absorption band to a longer wavelength. In consequence, this material has limited applicability in the case of, say, frequency doubling. For, it is inadvisable for the optically non-linear material to have absorption bands in the very working range in which frequency doubling is to be carried out: ordinarily, electromagnetic radiation having a wavelength of 700 to 1300 nanometers (nm) is passed through a frequency doubler by means of a laser, which results in a light source emitting a wavelength of half that length, i.e., in the range of approximately 350 to 650 nm. Preparing an optically non-linear active material without any absorption bands in the 350 to 650 nm range has proved to be a difficult affair.

A drawback to the conventional guest-host systems is that the stability of the poled films frequently leaves much to be desired. The effective non-linear coefficients ($d_{33}$) of the poled film were found to decrease after some time. The effective coefficient is indicative of the non-linear optical behavior of the film. It takes account of the hyperpolarizability of each optically non-linear active dopant molecule and the degree to which it contributes within the film to the overall non-linear optical behaviour. In addition, the solubility of the dopant in the optically transparent polymer frequently causes problems. In general, only up to 5 weight percent of dopant can be incorporated into the already known guest-host systems.

SUMMARY OF THE INVENTION

The present invention has for its object to obviate these drawbacks and provide an optically non-linear active waveguiding material comprising dopants of high hyperpolarizability. To this end, the invention consists in that the optically non-linear active dopant comprises more than one donor-$\pi$-acceptor unit.

DETAILED DESCRIPTION OF THE INVENTION

The dopant

By dopants comprising more than one donor-$\pi$-acceptor unit are meant, compounds containing multiple complete donor-$\pi$-acceptor units side by side. It was found that the charge-transfer absorption band wavelength of these compounds was about the same as for dopants with only one donor-$\pi$-acceptor unit.

Preferably, use is made of dopants in which the donor-$\pi$-acceptor units are positioned in a cyclic group. In this manner the donor-$\pi$-acceptor units' dipole moments provide optimum mutual reinforcement, giving maximum hyperpolarizability ($\beta$).

Suitable donor groups with which conjugated $\pi$-systems may be functionalised include: alkoxy groups, aryloxy groups, amino groups (—NR$_2$, —NHR, —NH$_2$), amido groups, provided that their coupling is via the nitrogen atom, hydroxyl groups (—NHCOR), —O—, —S—, ester groups, provided that their coupling is via the oxygen atom of the alcohol (—OCOR), thiol ethers (—SR), mercapto groups (—SH), halogens (F, Cl, Br, I), alkyl groups, and aryl groups. R in this case represents alkyl groups in general.

Suitable acceptor groups include: cyano groups, carboxylic acids, carboxylic esters, provided that their coupling is via the acidic carbon atom (—COOR), amido groups, provided their coupling is via the acidic carbon atom (—CONH$_2$, —CONHR, CONR$_2$), aldehyde groups, ketone groups, sulfonyl groups (—SO$_2$R, SO$_2$CH$_3$), sulfonate groups (—SO$_2$OR), nitro groups, substituted stilbene groups, such as nitrostilbene groups, cyanostilbene groups, and sulfonyl stilbene groups, substituted azo compounds, such as p-nitro azobenzene, cyano azobenzene, and sulfonyl azobenzene, substituted benzylidene aniline compounds such as cyanobenzylidene aniline, nitrobenzylidene aniline compounds, and aryl groups. Aryl groups may function as donors as well as acceptors.

Pre-eminently suitable dopants according to the invention were found to be calix(4)arenes. By this term are meant, cyclophanes composed of four phenol groups connected by methylene bridges. For more detailed information on calixarenes reference is made to "Calixarenes 12. The Synthesis of Functionalized Calixarenes" Gutsche and Lin *Tetrahedron*, Vol. 42 (1988), 1633–40. Functionalization with acceptor groups makes it possible for two to four donor-$\pi$-acceptor groups to be combined into a single calix(4)arene molecule. Alternatively, the hydroxyl groups may be replaced with other donor groups.

Calixarenes having more than one donor-acceptor unit (alkoxy/nitro) are known from JP 62 265 250. Azocalix(4)arenes having nitro groups at the lower rim and hydroxyl groups at the upper rim (defined in the next paragraph) are described in "Diazo-Coupling Reactions with Calix[4]rene. p$K_a$ Determination with Chromophoric Azocalix[4]arenes" Shinkai et al. *Chemistry Letters*, 1989, Tokyo JP, pp. 931–934, and in "Ipso Nitration of p-tert-Butylcalix[4]arenes" Verboom et al. *J. Chem. Soc. Perkin Trans I*, 1989, pp. 195–196. However, these publications refer to the possible use of these compounds as host molecules in solution which are capable of including small molecules or ions in their cavities. Said publications do not suggest the use of calix(4)arenes with donor-$\pi$-acceptor units as optically non-linear active dopants in waveguiding material.

Two types of reactive sites may be distinguished on a calix(4)arene molecule. The four hydroxyl groups together make up the lower rim of the calix(4)arene, while the para-positions of the four phenol rings form the upper rim. See formula 1.

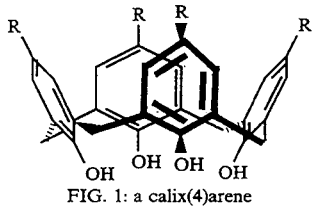

FIG. 1: a calix(4)arene

In order to form the donor-$\pi$-acceptor units, the reactive sites on the lower rim and the upper rim are functionalized with donor groups and acceptor groups, respectively.

In addition to displaying excellent hyperpolarizability, these compounds were found to be readily soluble in polymers. In particular, they were found to be readily soluble (up to 100 wt. %) in polymethyl methacrylate and polystyrene.

functionalization of the calix(4)arenes' lower rims

If for the substitution of the calix(4)arenes' OH-groups larger groups are employed than 2-hydroxyethyl, this will result in three different, non-interconvertible calix(4)arene conformations: the cone conformation (CONE) and two partial cone conformations (PACO). By establishing the appropriate reaction conditions while functionalizing the lower rim it is possible to obtain calix(4)arenes virtually exclusively in the cone conformation (above 90 mole-% yield). It was found that calix(4)arenes functionalized with donor groups and acceptor groups had a higher hyperpolarizability ($\beta$) in the cone conformation than in the partial cone conformation.

For instance, the alkylation of tert-butyl calix(4)arene in the presence of a strong base, such as NaH in N,N-dimethyl formamide (DMF) or acetonitrile at room temperature will give tetra-alkylated calix(4)arene, which is virtually exclusively in the cone conformation.

For more detailed information on the selective alkylation of calix(4)arenes reference is made to "syn-1,2-Dialkylated Calix[4]arenes: General Intermediates in the NaH/DMF Tetraalkylation of Calix[4]arenes", Groenen, et al *Tetrahydron Lett.*, Vol. 32, 2675–2678.

The phenolic OH-groups of calix(4)arenes can easily be replaced by thiol groups. Newman-Kwart rearrangement of the corresponding Odimethyl thiocarbamates produces S-dimethyl thiocarbamates, the reduction of which produces thiol groups.

By using calix(4)arenes, dehydroxylated calix(4)arenes (reductive cleavage reaction), or alkylated calix(4)arenes, other donor groups may be applied in manners familiar to the person of ordinary skill in the art.

Functionalization of the calix(4)arenes' upper rim

Both with calix(4)arenes substituted at the lower rim and in the case of those which still retain their OH-groups, acceptor groups can easily be introduced on the para-positions by, for instance, electrophilic substitution. These types of substitution reactions are known to the person of ordinary skill in the art and require no further elucidation here.

Pre-eminently suited to be used as dopants are calix(4)arenes which satisfy formula 2 below, since they are easy to prepare and highly soluble in the host polymers.

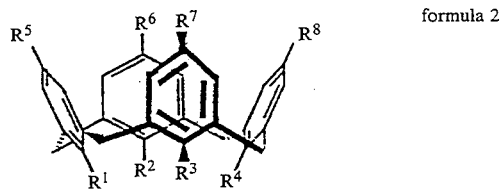

formula 2 wherein:

$R^1$ equals $R^3$ and/or $R^4$ and stands for: —O-alkyl having 1–30 carbon atoms, —NH$_2$, —NHR$^9$, —NR$^9$R$^9$, —NHCOR$^9$, —OH, —O$^-$, —SH, —S$^-$, SR$^9$, —OCOR$^9$, —F, —Cl, —I, —Br, —R$^9$, —R$^{10}$, $R^2$ equals $R^1$ or —H, —R, or —R$^{10}$, $R^3$ represents —H, —R$^9$, or —R$^{10}$ if $R^3$ does not equal $R^1$, $R^4$ represents —H, —R$^9$, or —R$^{10}$ if $R^4$ does not equal $R^1$, $R^9$ represents an alkyl group having 1–30 carbon atoms, $R^{10}$ represents an aryl group having 1–30 carbon atoms, $R^5$ equals $R^7$ if $R^1$ equals $R^3$; equals $R^8$ if $R^1$ equals $R^4$, and represents:

—NO$_2$, —CN, —R$^9$COOH, —R$^{10}$COOH, —R$^9$COONa, —R$^{10}$COONa, —COOR$^9$, —COOR$^{10}$, —CONH$_2$, —CONHR$^9$, —CONR$^9$R$^9$, —CONHR$^{10}$, an aldehyde group having 1–30 carbon atoms, a ketone group having 1–30 carbon atoms, —SO$_2$R$^9$, —SO$_2$OR$^9$, —SO$_2$R$^{10}$, —SO$_2$OR$^{10}$, a nitrostilbene group, a cyanostilbene group, a sulfonyl stilbene group, a sulfonate stilbene group, a nitroazo group, a cyanoazo group, a sulfonyl azo group, a sulfonate azo group, —CH=N—C$_6$H$_4$—NO$_2$, —CH=N—C$_6$R$^9$H$_3$—NO$_2$, —CH=N—C$_6$H$_4$—CN, —CH=N—C$_6$R$^9$H$_3$—CN, —H=N—C$_6$-

$H_4$—$SO_2$, —CH=N—$C_6R^9H_3$—$SO_2$, —CH=N—$C_6H_4$—$SO_2O$, —CH=N—$C_6R^9H_3$—$SO_2O$, —N=CH—$C_6H_4$—$NO_2$, —N=CH—$C_6R^9H_3$—$NO_2$, —N=CH—$C_6H_4$—CN, —N=CH—$C_6R^9H_3$—CN, —N=CH—$C_6H_4$—$SO_2$, —N=CH—$C_6R^9H_3$—$SO_2$, —N=CH—$C_6H_4$—$SO_2O$, —N=CH—$C_6R^9H_3$—$SO_2O$, —$R_{10}$, and $R^6$ equals $R^5$ and or has the meaning of an H-atom,
$R^7$ represents —H if $R^7$ does not equal $R^5$,
$R^8$ represents —H if $R^8$ does not equal $R^5$.

In the case of stilbenes, azobenzenes, and benzylidene anilines one of the phenyl groups will always be part of the calix(4)arene.

The tert-butyl groups of calix(4)arenes substituted therewith may be replaced by nitro groups by means of so-called IPSO-nitration. For more detailed information on this reaction reference is made to "Ipso Nitration of p-tert-Butylcalix[4]arenes", Verboom, et al. *J. Org. Chem.*, Vol. 57(4), 1313–1316 (1992).

Nitro-functionalized calix(4)arenes, notably tetranitrofunctionalized calix(4)arenes, are preferred for their charge-transfer absorption band at a low wavelength ($\lambda_{max}$ at about 300 nm). Aldehyde-functionalized calix(4)arenes were also found to have this low-wavelength charge-transfer absorption band ($\lambda_{max}$ at about 270 nm). In consequence, optically non-linear active waveguiding material comprising these dopants is pre-eminently suited to be used for frequency doubling, e.g., for frequency doublers which generate blue light. Calix(4)arenes satisfying formula 3 below therefore are especially preferred.

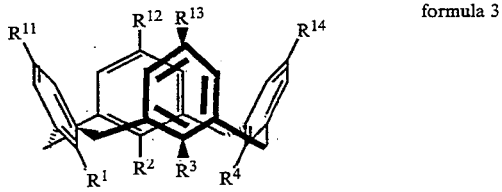

formula 3 wherein:
$R^1$ equals $R^3$ and/or $R^4$ and stands for:
—O-alkyl having 1–30 carbon atoms, —$NH_2$, —$NHR^9$, —$NR^9R^9$, —$NHCOR^9$, —OH, —$O^-$, —SH, —$S^-$, $SR^9$, —$OCOR^9$, —F, —Cl, —I, —Br, —$R^9$, —$R^{10}$, —O—$R^{10}$, $R^2$ equals $R^1$ or —H, —$R^9$, or —$R^{10}$,
$R^3$ represents —H, —$R^9$ or —$R^{10}$ if $R^3$ does not equal $R^1$,
$R^4$ represents —H, —R, or —$R^{10}$ if $R^4$ does not equal $R^1$,
$R^9$ represents an alkyl group having 1–30 carbon atoms,
$R^{10}$ represents an aryl group having 1–30 carbon atoms,
$R^{11}$ equals $R^{13}$ if $R^1$ equals $R^3$; equals $R^{14}$ if $R^1$ equals $R^4$, and has the meaning of:
—$NO_2$ or an aldehyde group having 1–30 carbon atoms, and
$R^{12}$ equals $R^{11}$ and or has the meaning of an H-atom,
$R^{13}$ represents —H if $R^{13}$ does not equal $R^{11}$,
$R^{14}$ represents —H if $R^{14}$ does not equal $R^{11}$.

In addition, the invention relates to hitherto undisclosed calix(4)arenes which are pre-eminently suitable for use as optically non-linear active dopants. Meant here are calix(4)arenes functionalized with nitrostilbene groups, cyanostilbene groups, sulfonyl stilbene groups, sulfonate stilbene groups, or benzylidene aniline compounds, and satisfying formula 4 below. In the case of stilbenes and benzylidene anilines one of the phenyl groups will always be part of the calix(4)arene.

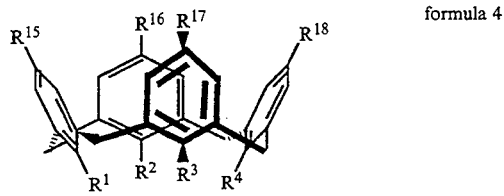

formula 4 wherein:
$R_1$ equals $R^3$ and/or $R^4$ and stands for:
—O-alkyl having 1–30 carbon atoms, —$NH_2$, —$NHR^9$, —$NR^9R^9$, —$NHCOR^9$, —OH, —$O^-$, —SH, —$S^-$, $SR^9$, —$OCOR^9$, —F, —Cl, —I, —Br, —$R^9$, —$R^{10}$, —O—$R^{10}$, $R^2$ equals $R^1$ or —H, —$R^9$ or —$R^{10}$,
$R^3$ represents —H, —$R^9$ or —$R^{10}$ if $R^3$ does not equal $R^1$,
$R^4$ represents —H, —$R^9$ or —$R^{10}$ if $R^4$ does not equal $R^1$,
$R^9$ represents an alkyl group having 1–30 carbon atoms,
$R^{10}$ represents an aryl group having 1–30 carbon atoms,
$R^{15}$ equals $R^{17}$ if $R^1$ equals $R^3$; equals $R^{18}$ if $R^1$ equals $R^4$, and represents:
a nitrostilbene group, a cyanostilbene group, a sulfonyl stilbene group, a sulfonate stilbene group, , —CH=N—$C_6H_4$—$NO_2$, —CH=N—$C_6R^9H_3$—$NO_2$, —CH=N—$C_6H_4$—CN, —CH=N—$C_6R^9H_3$—$NO_2$, —CH=N—$C_6H_4$—$SO_2$, —CH=N—$C_6R^9H_3$—$SO_2$, —CH=N—$C_6H_4$—$SO_2O$, —CH=N—$C_6R^9H_3$—$SO_2$), —N=CH—$C_6H_4$—$NO_2$, —N=CH—$C_6R^9H_3$—$NO_2$, —N=CH—$C_6H_4$—CN, —N=CH—$C_6R^9H_3$—CN, —N=CH—$C_6H_4$—$SO_2$, —N=CH—$C_6R^9H_3$—$SO_2$, —N=CH—$C_6H_4$—$SO_2O$, —N=CH—$C_6R^9H_3$—$SO_2O$, $R^{16}$ equals $R^{15}$ or has the meaning of an H-atom,
$R^{17}$ represents —H if $R^{17}$ does not equal $R^{15}$, and
$R^{18}$ represents —H if $R^{18}$ does not equal $R^{15}$.

These calix(4)arenes were found to have an extremely high hyperpolarizability. In consequence, optically non-linear active waveguiding material comprising such dopants is pre-eminently suited to be used as an optical switch.

In addition to having an extremely high hyperpolarizability, the calix(4)arenes containing cyanostilbene groups and sulfonyl stilbene groups were found to have a narrow charge-transfer absorption band ending at 450 and 395 nm, respectively. This means that optically non-linear active waveguiding material containing such dopants is also suitable for use as a frequency doubler. Consequently, particular preference is giving to these calix(4)arenes being employed.

The host polymer

In principle, all optically transparant polymers that can be used in polymeric optical waveguides in the ordinary course of events may serve as hosts to an optically non-linear active dopant according to the invention. Examples of such polymers include polyalkylene acrylates, notably polymethyl (meth)acrylate, polycarbonates, polyesters, polystyrene, and fluor- and/or chlorine-containing polymers, notably vinylidene difluoride polymers. Preference is given to the use of polymethyl methacrylate or polystyrene, since these polymers constitute superior media for dissolving the dopants.

Generally, waveguiding structures are shaped like a flat waveguide with a so-called sandwich structure. The person of average skill in the art will be familiar with the composition and preparation thereof, which require no further elucidation here. The optically non-linear active dopants according, to the invention can easily be admixed with the host polymer prior to the forming of a film thereof on a substrate.

The invention will be further illustrated with reference to several unlimitative examples.

EXAMPLES

Examples 1 and 2:

Preparation of tetrapropylated tetranitrocalix(4)arene (cf. Diagram 1)

To a solution of 3.00 mmoles of tetrapropylated tert-butyl calix(4)arene (CONE conformation) in a mixture of 30 ml of $CH_2Cl_2$ and 30 ml of glacial acetic acid 10 ml of 100% $HNO_3$ were added at 0° C. The reaction mixture was stirred at room temperature until it had lost its purplish black colour, after which it was poured in 200 ml of water. The aqueous layer was extracted twice, with 50 ml of $CH_2Cl_2$ being used each time. The combined organic layers were washed with water (twice, with 50 ml being used each time), dried on $MgSO_4$, and concentrated. Recrystallization of the crude product from dichloromethane/methanol yielded the product in the pure form (calix(4)arene 1).

The same reaction was carried out making use of tetrapropylated tert-butyl calix(4)arene in PACO conformation (calix(4)arene 2).

Examples 3, 4, and 5

Preparation of tetrapropylated mononitro calix(4)arene and tetrapropylated dinitro calix(4)arene (cf. Diagram 1)

To a solution of 1.7 mmoles of calix(4)arene in a mixture of 100 ml of $CH_2Cl_2$ and 4 ml of glacial acetic acid was added 1 ml of 65% $HNO_3$, after which the mixture was stirred for 30 minutes at room temperature. The reaction was stopped by the addition of 100 ml of water, and the product mixture was extracted with $CH_2Cl_2$ (three times, using 25 ml each time). The combined organic layers were washed with water (three times), saturated sodium bicarbonate solution (three times), and water (three times), with 25 ml of the respective liquid being used each time, dried on $MgSO_4$, and concentrated. The reaction mixture was composed mostly of mononitro calix(4)arene (30 mole %, calix(4)arene 4) and traces of 1,3-dinitro calix(4)arene and 1,2-dinitro calix(4)arene.

Carrying out the same reaction over a period of three hours gave a yield of 30 wt. % of 1,3-dinitro calixarene (calix(4)arene 4) and 10 wt. % of 1,2-dinitro calix(4)arene (calix(4)arene 5).

The different products were separated by column chromatography. ($SiO_2/CH_2Cl_2$).

Examples 6, 7, 8, and 9

Preparation of tetra-alkylated aldehyde calix(4)arenes (cf. Diagram 2)

To a solution of tetrapropylated calix(4)arene in $CHCl_3$ were added at $-10°$ C. 10 eq. of $SnCl_4$ and 10 eq. of $CHCl_2OCH_3$. The reaction mixture was stirred for 10 minutes. After purification a yield of 30 wt. % of tetrapropylated monoethanal calix(4)arene (calix(4)arene 6) was obtained.

For the preparation of calix(4)arenes 7, 8, and 9 reference is made to Diagram 2. For the preparation of calix(4)arene 7 use was made of tetra-ethoxyethylated calix(4)arene, R in this formula standing for $CH_3CH_2OCH_2CH_2-$.

Examples 10 and 11

Preparation of tetrapropylated nitrostilbene calix(4)arenes (cf. Diagram 3)

Using tetrapropylated ethanal calix(4)arenes, tetrapropylated nitrostilbene calix(4)arenes were prepared as specified in Diagram 3 (calix(4)arenes 10 and 11).

Example 12

Preparation of tetranitroazo calix(4)arene (cf. Diagram 4)

Using calix(4)arene, tetranitroazo calix(4)arene was prepared as specified in Diagram 4 (calix(4)arene 12).

The dipole moment of all of the prepared calix(4)arenes was determined by measuring the dielectric constant of the solutions with a capacitance bridge. The dipole moments ($\mu$ in Debye $= 3.33564 * 10^{-30}$ C.m) are compiled in TABLES I, II, III, and IV. These tables also list the charge-transfer absorption bands ($\lambda_{max}$ measured in chloroform, in nm).

The hyperpolarizability ($\beta$) was measured by means of "electric field induced second harmonic generation" (EFISH). The source of radiation used was an 1.064 $\mu$m 10 Hz pulsed Nd/YAG laser with seeder. The laser beam was passed through an RG830 visible light filter and focussed on the EFISH cell. The harmonic light was detected with the aid of a photomultiplier tube and analyzed. The EFISH cell consisted of two BK7 windows forming a wedge with an angle of about 1°. The distance between the windows was 0.1–0.2 mm, the distance between the high voltage electrodes was 3 mm. Measuring the second harmonic intensity as a function of the path length gave a sinusoidal interference pattern, a quartz wedge being used as reference. The hyperpolarizabilities ($\beta$ in esu $= 4.19 * 10^{-10}$ m$^4$/V) are given in TABLES I, II, III, and IV.

The calix(4)arenes were mixed into a solution of polymethyl methacrylate in chloroform, and by means of spin coating a thin film was applied onto an ITO electrodes coated glass substrate or a pyrex substrate. The film had a thickness of about 0.25 $\mu$m. After a 10-minute heat treatment the films were poled in a Corona discharge (10 kV) at 110° C. for 15 minutes. The effective non-linear coefficients ($d_{33}$) were determined using an $\alpha$-quartz crystal ($d_{11} = 0.51$ pm/V at 1064 nm) with a 1 mm cut in the z-direction as a reference. The source of fundamental radiation used was an Nd/YAG laser combined with a dye laser. A Soleil-Babinet compensator was used to correct the polarization of the fundamental beam. The sample was rotated in the laser beam, its rotation axis being kept perpendicular to the incident polarization direction. Filters were used to separate the harmonic and the fundamental radiation.

All of the prepared films were found to display non-linear optical activity after being poled. (The effective coefficients ($d_{33}$) of films of 4.5 wt. % and 25 wt. % of calix(4)arene 1, respectively, were 0.21 and 1.1 pm/V. After ten days, the effective non-linear coefficient ($d_{33}$) of all films, independent of their dopant concentration, was found to have decreased to 65% of the original value. However, there was no further decrease of this value over the next six months. This shows that the poled films composed of optically non-linear active material according to the invention are highly stable.

TABLE I

| | nitrocalix(4) arenes | | |
|---|---|---|---|
| calix(4)arene | $\beta$ (in $10^{-30}$ esu) | $\lambda_{max}$ (in nanometers) | $\mu$ (in D) |
| 1 | 30 | 291 | 13.8 |
| 2 | 27 | 291 | 6.7 |
| 3 | 16 | 308 | 4.5 |
| 4 | 15 | 302 | 7.8 |
| 5 | 20 | 307 | 8.7 |

TABLE II

| | aldehyde calix(4)arenes | | |
|---|---|---|---|
| calix(4)arene | $\beta$ (in $10^{-30}$ esu) | $\lambda_{max}$ (in nanometers) | $\mu$ (in D) |
| 6 | 18 | 274 | 4.2 |
| 7 | 17 | 277 | 6.8 |
| 8 | 15 | 272 | 7.9 |
| 9 | 19 | 269 | 10.7 |

TABLE III

| | stilbene calix(4)arenes | | |
|---|---|---|---|
| calix(4)arene | $\beta$ (in $10^{-30}$ esu) | $\lambda_{max}$ (in nanometers) | $\mu$ (in D) |
| 10 *) | 222 | 376 | 0.5 |
| 11 | 280 | 370 | 15.3 |

*) This is trinotostilbene calix(4)arene, which is not depicted in Diagram 3.

TABLE IV

| | azocalix(4)arene | | |
|---|---|---|---|
| calix(4)arene | $\beta$ (in $10^{-30}$ esu) | $\lambda$max (in nanometers) | $\mu$ (in D) |
| 12 | 142 | 356 | 13.0 |

Diagram 1: nitration

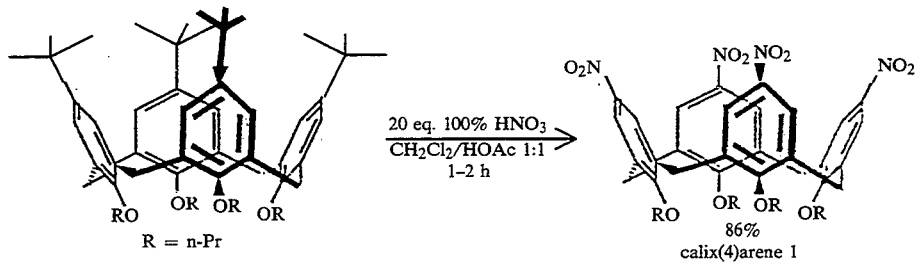

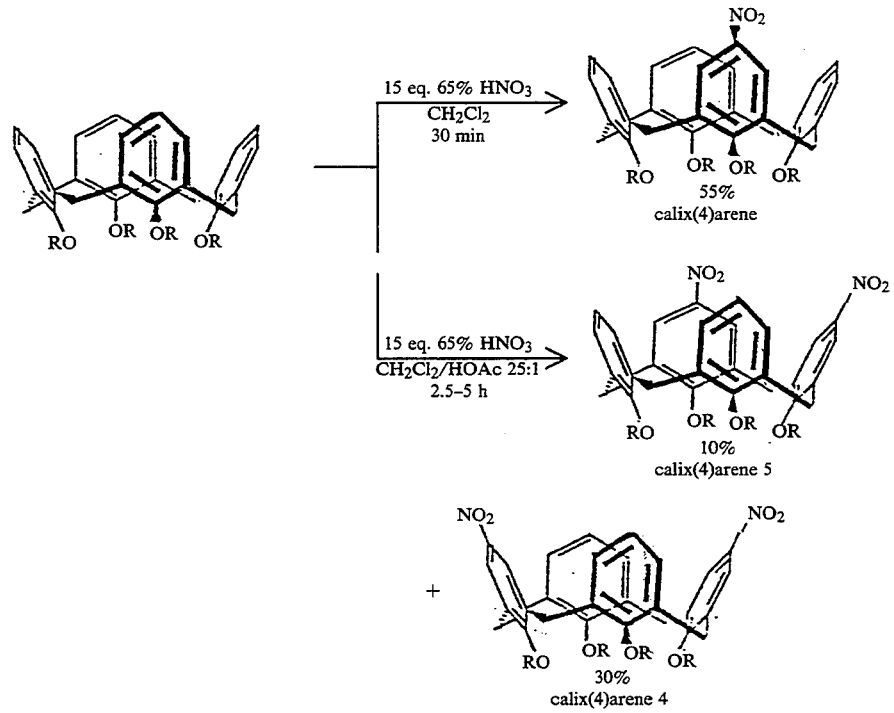

Diagram 2: formylation

-continued
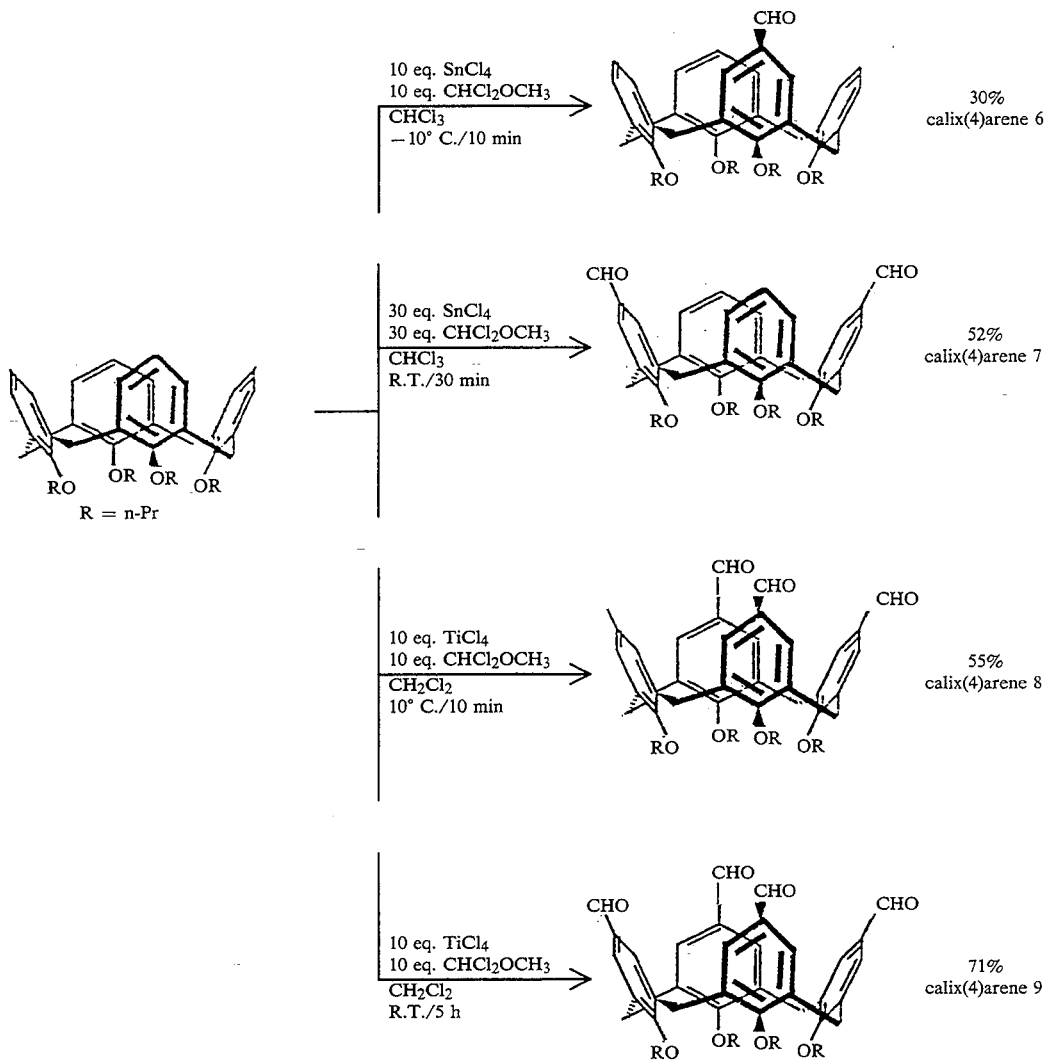
Diagram 3: synthesis of nitrostilbenes
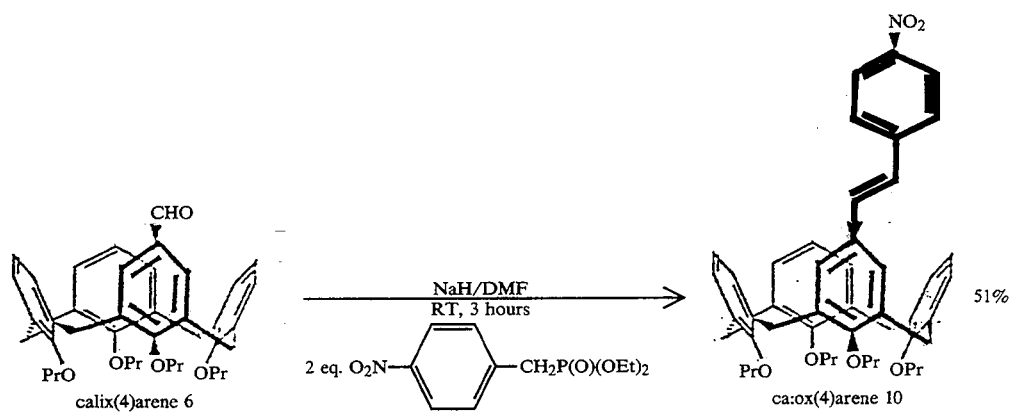

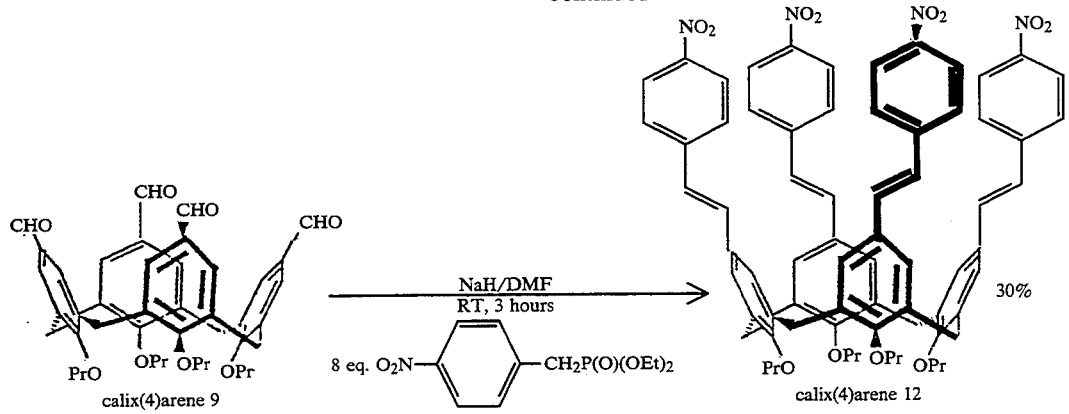

Diagram 4: synthesis of nitroazo calix(4)arene

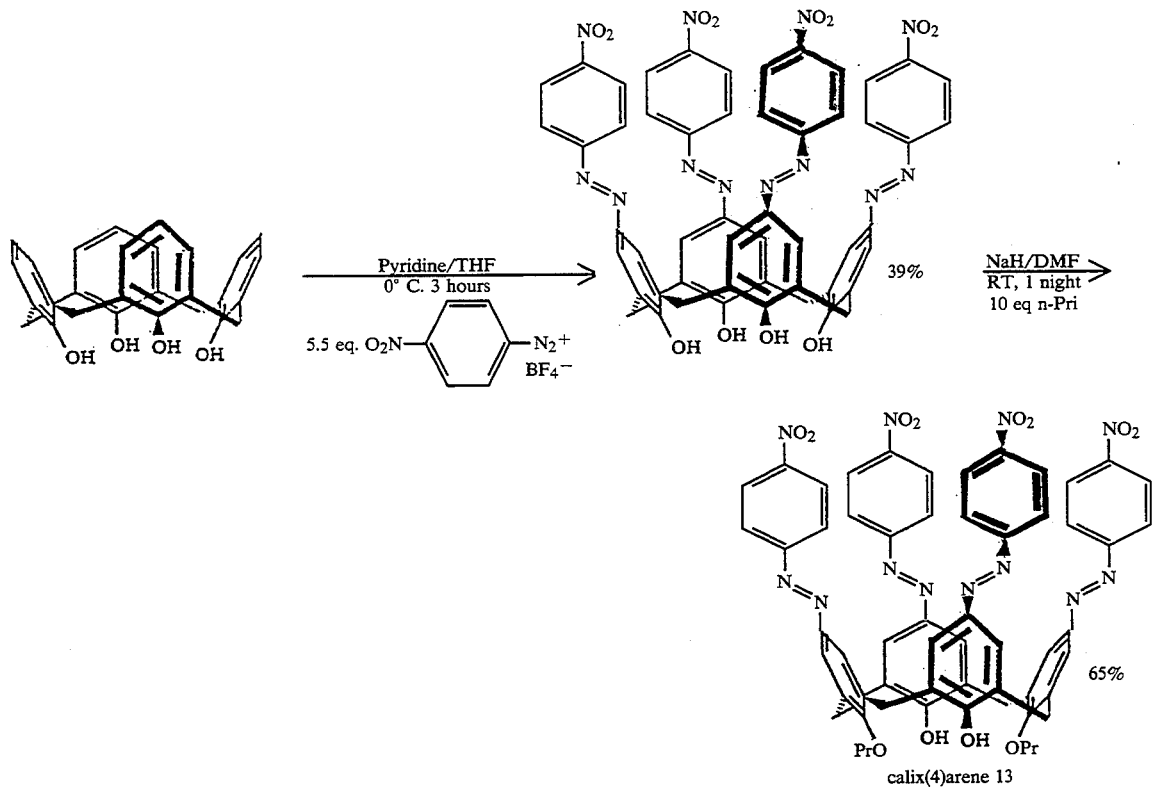

We claim:

1. An optically non-linear active waveguiding material comprising an optically transparent polymer and a non-linear optical dopant comprising a donor-π-acceptor unit wherein the non-linear optical dopant comprises a calix(4)arene which satisfies formula 3:

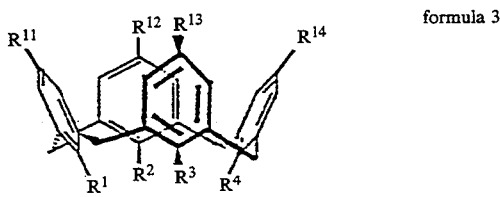

wherein:
$R^1$ equals $R^3$ and/or $R^4$ and stands for:
—O—alkyl having 1–30 carbon atoms, —NH$_2$, —NHR$^9$, —NR$^9$R$^9$, —NHCOR$^9$, —OH, —O$^-$, —SH, —S$^-$, SR$^9$, —OCOR$^9$, —F, —Cl, —I, —Br, —R$^9$, —R$^{10}$, —O—R$^{10}$, $R^2$ equals $R^1$ or —H, —R$^9$ or —R$^{10}$, $R^3$ represents —H, —R$^9$ or —R$^{10}$ if $R^3$ does not equal $R^1$, $R^4$ represents —H, —R$^9$ or —R$^{10}$ if $R^4$ does not equal $R^1$, $R^9$ represents an alkyl group having 1–30 carbon atoms, $R^{10}$ represents an aryl group having 1–30 carbon atoms, $R^{11}$ equals $R^{13}$ if $R^1$ equals $R^3$; equals $R^{14}$ if $R^1$ equals $R^4$, and has the meaning of:
—NO$_2$ or an aldehyde group having 1–30 carbon atoms, and $R^{13}$ equals $R^{11}$ or has the meaning of an H-atom, $R^{13}$ represents —H if $R^{13}$ does not equal $R^{11}$, and $R^{14}$ represents —H if $R^{14}$ does not equal $R^{11}$.

* * * * *